(12) United States Patent
An et al.

(10) Patent No.: US 6,241,757 B1
(45) Date of Patent: Jun. 5, 2001

(54) STENT FOR EXPANDING BODY'S LUMEN

(75) Inventors: Sung Soon An, Seoul; Chel Seng Kim, Cheollabuk-Do; Sung Pil Choi, Kyounggi-Do; Tae Hyung Kim; Ho Young Song, both of Seoul; Sang Woo Song, Cheollubuk-Do, all of (KR)

(73) Assignee: Solco Surgical Instrument Co., Ltd., Kyounggi-Do (KR)

( * ) Notice: Subject to any disclaimer, the term of this patent is extended or adjusted under 35 U.S.C. 154(b) by 0 days.

(21) Appl. No.: 09/017,773

(22) Filed: Feb. 3, 1998

(30) Foreign Application Priority Data

| Apr. 2, 1997 | (KR) | 97-3409 |
| Jul. 10, 1997 | (KR) | 97-51355 |
| Jul. 1, 1998 | (KR) | 98-182 |

(51) Int. Cl.⁷ .................................................. A61F 2/06
(52) U.S. Cl. ............................................ 623/1.1; 623/1.5
(58) Field of Search ................................ 623/1, 12, 1.1, 623/1.15, 1.16, 1.17, 1.32, 1.33; 606/198, 195, 194

(56) References Cited

U.S. PATENT DOCUMENTS

| 4,214,587 | | 7/1980 | Sakura, Jr. .................... 128/334 R |
| 4,580,568 | | 4/1986 | Gianturco ........................ 128/345 |
| 4,655,771 | | 4/1987 | Wallsten .............................. 623/1 |
| 5,330,500 | | 7/1994 | Song et al. ...................... 606/198 |
| 5,366,504 | * | 11/1994 | Anderson et al. .................. 623/11 |
| 5,545,211 | * | 8/1996 | An et al. ............................... 623/1 |
| 5,782,904 | * | 7/1998 | White et al. ...................... 623/1 X |
| 5,833,707 | * | 11/1998 | McIntyre et al. .............. 606/198 X |
| 5,876,445 | * | 4/1999 | Anderson et al. .................. 623/11 |
| 5,919,225 | * | 7/1999 | Lau et al. .............................. 623/1 |
| 5,948,018 | * | 9/1999 | Dereume et al. .................... 623/1 |

FOREIGN PATENT DOCUMENTS

| WO 92/06734 | 4/1992 | (WO) . |
| WO 93/13825 | 7/1993 | (WO) . |

\* cited by examiner

*Primary Examiner*—V. Millin
*Assistant Examiner*—Hien Phan
(74) *Attorney, Agent, or Firm*—Graybeal Jackson Haley LLP

(57) ABSTRACT

A stent for expanding a lumen of a body having a structural stability along the length of the stent, as well as a good expandable force. According to one embodiment of the present invention, the stent is made of a single length of a filament and includes zigzag sections, in which the filament is wound in a zigzag manner, disposed on both end portions of the stent; and a spiral section, in which the filament is wound in a spiral manner, disposed between the zigzag sections. The zigzag section includes a plurality of bands. Each of the bands includes a series of straight portions, peak portions, and valley portions, the peak and valley portions being integrally engaged with the straight portions, and each of the bands is disposed along a circumferential direction of the stent on a plane substantially perpendicular to a longitudinal axis thereof; and each valley portion of the bands is twisted with a peak portion of an adjacent band. Also, the spiral section includes a body portion formed in such a way that the filament crosses in a spiral pattern to form a plurality of segments with the filament being not engaged with each other, and upper and lower end portions having a plurality of bent points.

32 Claims, 12 Drawing Sheets

STENT FOR EXPANDING BODY'S LUMEN

BACKGROUND OF THE INVENTION

1. Field of the Invention

The present invention relates to a stent for expanding a lumen of a body.

2. Description of the Prior Art

It is desirable in various situations that means has to be provided for expanding a constricted vessel portion or for maintaining an open passageway through a vessel portion.

For example, these situations can be those by malignant esophageal strictures that are caused by esophageal carcinoma or esophageal metastasis, those by benign strictures that are caused by operation or cauterant esophagitis, or those by strictures of blood vessel system, biliary system, lachrymal duct system, urinary duct system and bronchial system.

The balloon expansion has been a well-known method of enlarging and maintaining the strictured site in these cases. However, such method has a disadvantage in that it is used repeatedly on a patient due to its temporary effects, and it has no effects on the patients of serious strictures.

As alternatives, various artificial-esophagi have been used in the cases of esophageal strictures, but since they have no constriction and relaxation, the rate of esophageal rupture is high (30–40%) in the process of inserting them into the strictured site that has been caused by cancer, and the high mortality rate due to mediastinitis results from rupture of an esophagus. In addition, the patient has a great difficulty in swallowing due to a narrow inner diameter (10–12 mm) of artificial esophagus, and obstruction of an artificial esophagus occurred frequently due to food intakes.

As the means of overcoming the difficulty, a device to hold the passageway enlarged using a stent was presented by U.S. Pat. No. 4,214,587. However, so the device of the invention has the temporary effect in enlarging the passageway, there is still the problem that the endovascular lumen gets narrows after a long time.

To improve this disadvantages, U.S. Pat. No. 4,580,568 discloses a stent including a wire formed into a closed zigzag configuration including an endless series of straight sections joined by bends. The stent is resiliently compressible into a smaller first shape wherein the straight sections are arranged side-by-side and closely adjacent one another for insertion, and into a larger second shape wherein the straight sections press against the walls of the passageway to maintain it open.

Self-expandable stents are normally evaluated with respect to four performance characteristics: the radially outward expandable force that the stent exerts on the vascular wall; the small diameter to which the stent is capable of being compressed for the insertion procedure; the ability of the stent to adapt to curved passageways in the patient's body; and the stability of the stent in not migrating from its originally implanted position within the patient.

Conventional zigzag stents must normally be made relatively short because the straight wire sections prevent the stent from readily adapting to curves in the passageway of a patient. Furthermore, the expandable force of conventional zigzag stents generally decreases with the length of the stent. One solution to these drawbacks has been to modify the conventional zigzag stent by connecting a plurality of shorter stents end on end to create one longer zigzag stent assembly. Although these modified zigzag stents for certain applications, there exists a need for an elongated self-expandable stent that includes the advantages of both conventional and modified zigzag stents but which has improved performance characteristics over both.

To solve these problems, a number of stents have been developed, wherein there are stents of Wall-type and Cook-type as a typical one among them.

International Publication No. WO 93/13825 discloses an example of the Cook type of stent. The self-expandable stent disclosed in the Publication includes a wire bent into an elongated zigzag pattern having a plurality of substantially straight wire sections separating a plurality of bends, and a plurality of filaments for interconnecting adjacent bends of the helix. The elongated zigzag pattern is helically wound about a center axis to define a tubular shape such that a majority of the plurality of bends is disposed in a helix. There is a drawback in that the stent has a good expanding force but poor structural stability, because the plurality of filaments is interconnected each other into a zigzag pattern.

U.S. Pat. No. 4,655,771 discloses an example of the Wall type of stent. The stent disclosed in the patent has a radial and axially flexible, elastic tubular body with a predetermined diameter that is variable under axial movement of ends of the body relative to each other and which is composed of a plurality of individually rigid but flexible and elastic thread elements each of which extends in a helix configuration along the center line of the body as a common axis, the flexible and elastic elements defining radially self-expanding body. The body includes a first number of elements having a common direction of winding but be axially displaced relative to each other, and crossing a second number of elements also axially displaced relative to each other but having an opposite direction of winding, the crossing of the first and second elements defining at least an obtuse angle. The stent has a uniform and stable structure, but has a disadvantage that the expandable force deteriorates at some extent. In addition, the zigzag pattern stent generally shortens axially as it radially expands.

SUMMARY OF THE INVENTION

In view of the problems involved in the prior art, it is an object of the present invention to provide a stent for expanding a lumen of a body having a structural stability along the length of the stent, as well as a good expandable force.

Another object of the present invention is to provide a stent for expanding a lumen of a body capable of expanding a strictured site and maintaining an open passageway through the lumen for a long period, without migrating inside the lumen.

A further object of the present invention is to provide a stent for expanding a lumen of a body having an even performance along the length of the stent to easily adapt to the curved passageways of a lumen.

A still further object of the present invention is to provide to a stent for expanding a lumen of a body having an improved stability which maintains the position of the stent in the lumen of the patient.

In order to achieve the above objects, according to one aspect of the present invention, there is provided a stent for expanding a lumen of a body, the stent being made up of a single length of a filament and including a plurality of bands formed in a zigzag pattern, wherein: each of the bands includes a series of straight portions, peak portions, and valley portions, the peak and valley portions being integrally engaged with the straight portions, and each of the bands is disposed along a circumferential direction of the stent on a plane substantially perpendicular to a longitudinal axis thereof; each valley portion of the bands is twisted with a peak portion of an adjacent band; and an initial portion of the filament is an extension from a last straight portion of a previous adjacent band.

According to another aspect of the present invention, there in provided a stent for expanding a lumen of a body, the stent being made of a single length of a filament, the stent comprising: a body portion formed in such a way that the filament crosses in a spiral pattern to form a plurality of segments with the filament being not engaged with each other; and upper and lower end portions having a plurality of bent points; wherein the number of the bent points of the upper end portion is equal with the number of the bent points of the lower end portion, and any one segment passes on and under other segments which are wound along a longitudinal axis of the stent in a spiral direction so that cross points of the segments form a plurality of meshes.

According to further another aspect of the present invention, there is provided a stent for expanding a lumen of a body, the stent being made of a single length of a filament, the stent comprising: zigzag sections, in which the filament is wound in a zigzag manner, disposed on both end portions of the stent; and a spiral section, in which the filament is wound in a spiral manner, disposed between the zigzag sections. The zigzag section comprised a plurality of bands. Each of the bands includes a series of straight portions, peak portions, and valley portions, the peak and valley portions being integrally engaged with the straight portions, and each of the bands is disposed along a circumferential direction of the stent on a plane substantially perpendicular to a longitudinal axis thereof; and each valley portion of the bands is twisted with a peak portion of an adjacent band. Also, the spiral section comprises a body portion formed in such a way that the filament crosses in a spiral pattern to form a plurality of segments with the segments being not engaged with each other; and upper and lower end portions having a plurality of bent points.

In the aspects of the present invention, the end portions of the stent have a flare shape in which a diameter is increased toward a distal end thereof, or have a larger diameter than the middle portion to prevent the stent from migrating inside the lumen. Also, the filament is made of a Ni—Ti alloy.

BRIEF DESCRIPTION OF THE DRAWINGS

The above objects, other aspects, and advantages of the invention will become apparent by describing the preferred embodiments thereof with reference to the accompanying drawings, in which.

DETAILED DESCRIPTION OF THE PREFERRED EMBODIMENTS

Figure 1:
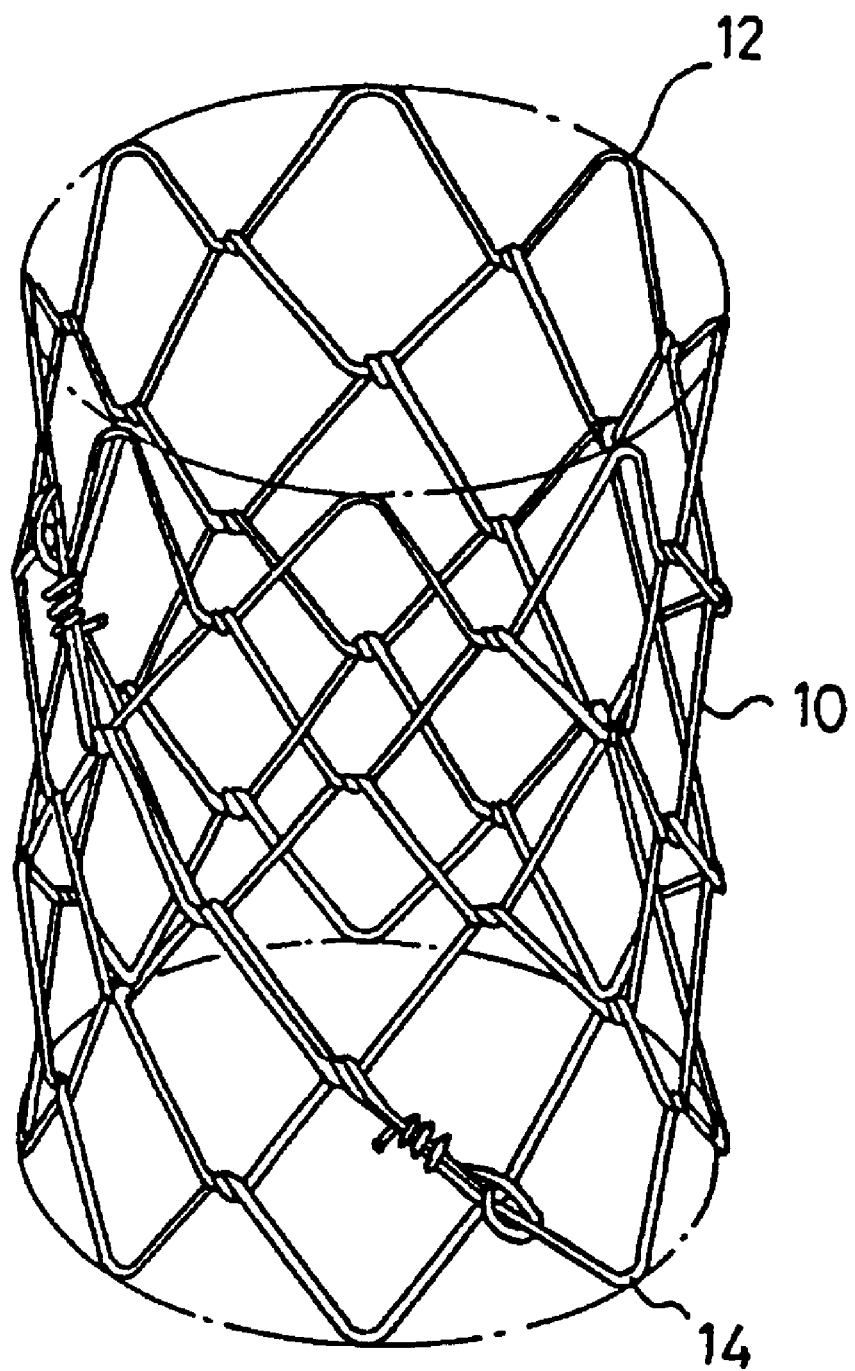
FIGS. 1 and 2 are perspective views showing the structure of a stent for expanding a lumen according to a first preferred embodiment of the present invention.
Figure 2:
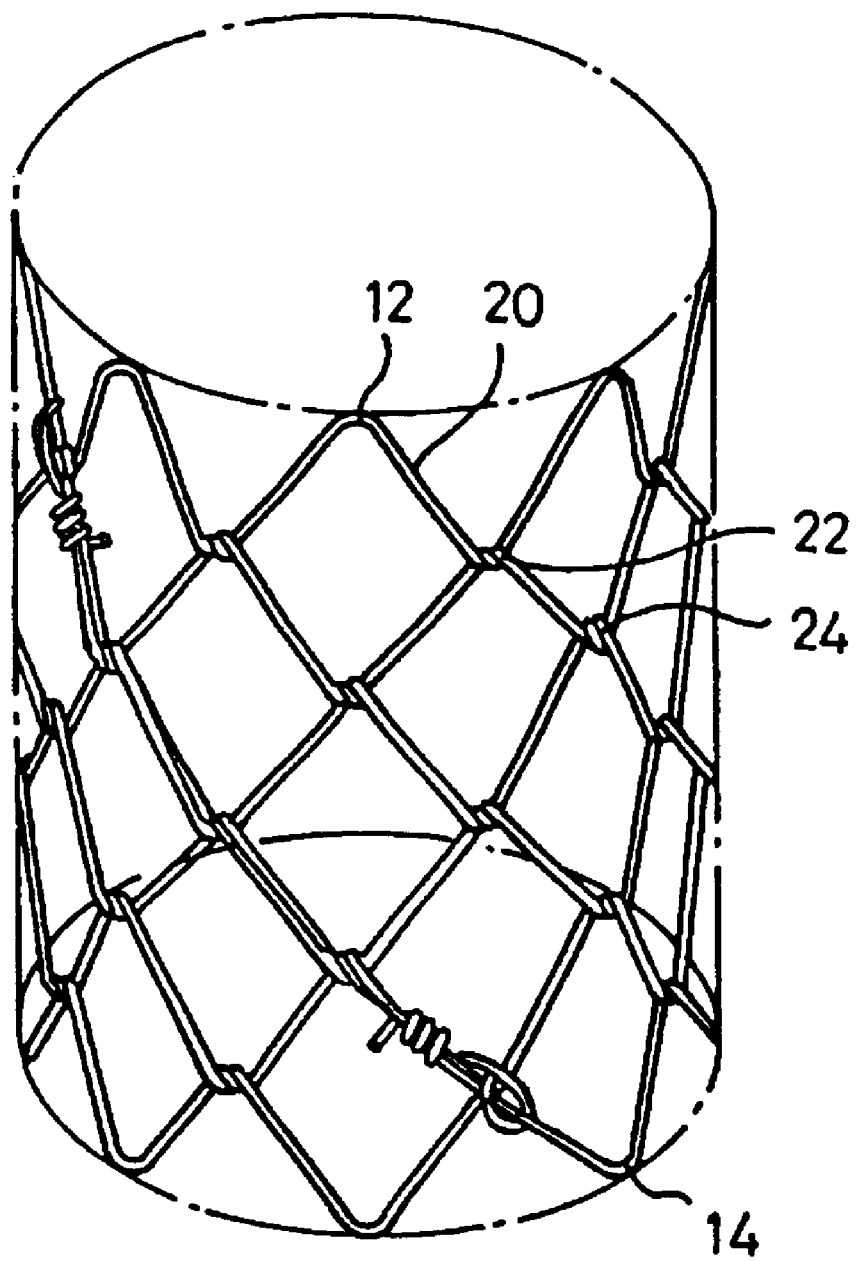

FIGS. 1 and 2 show perspectively a cylindrical stent according to a first preferred embodiment of the present invention, which is consisted of a single length of filament 10. Both distal ends of the cylindrical stent are of a plurality of bent points 12 and 14, with the bent points 12 and 14 being disposed on a plane substantially perpendicular to a longitudinal axis of the stent, respectively. This disposition may allow a diameter enlarging portion to form on the end of the stent, as will be described below. U.S. Pat. No. 5,545,211 issued to An et al on Aug. 13, 1996 discloses a stent including distal ends having a plurality of bent points slanted at a given helix angle, i.e., distributed in a helix along the length of the stent.

Figure 3:
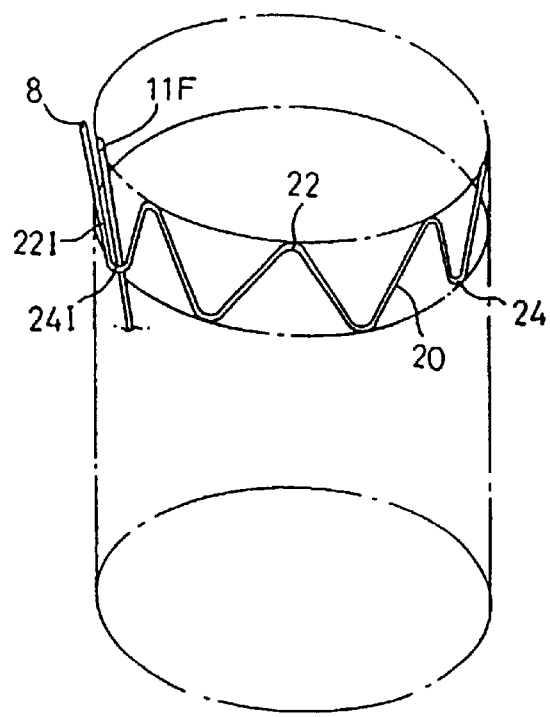
FIGS. 3 and 4 are views showing the manufacturing process of the stent of the first embodiment.

Referring to FIG. 2, the filament 10 is deposed in a zigzag pattern along a circumferential direction of the stent to form a band. The band includes a plurality of straight portions 20, a plurality of peak portions 22 (the term "peak portion" used therein refers to a portion protruding upwardly as will be seen in the drawing) and a plurality of valley portions 24 (the term "valley portion" used therein refers to a portion protruding downwardly as will be seen in the drawing), which the peak and valley portions are integrally connected by the straight portions 20. The continuous straight portions 20, peak portions 22 and valley portions 24 form a single band as shown in FIG. 3. The stent according to the first preferred embodiment of the present invention is formed by interconnecting bands.

Figure 4:
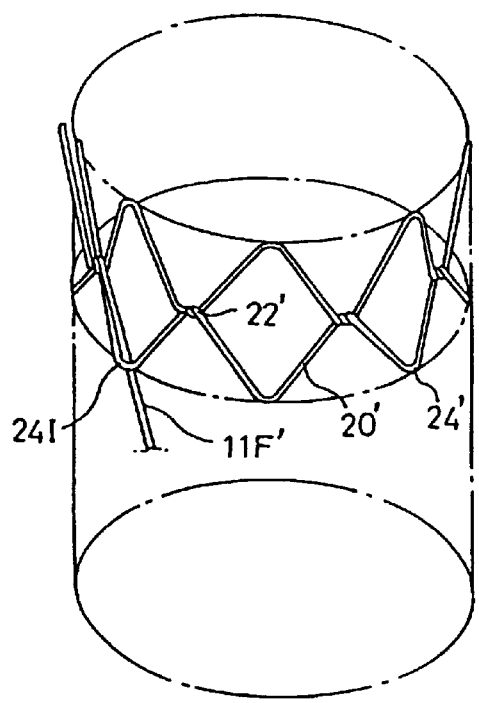

Referring to FIG. 4, the bends are interconnected in such a manner that the valley portions of the first band are twisted with the peak portions of the second adjacent band which is positioned underneath the first band. In order to easy this interconnection, and to prevent the shape of the stent from distorting when the expansion or contraction of it, the valley portions have substantially straight line.

Figure 12:
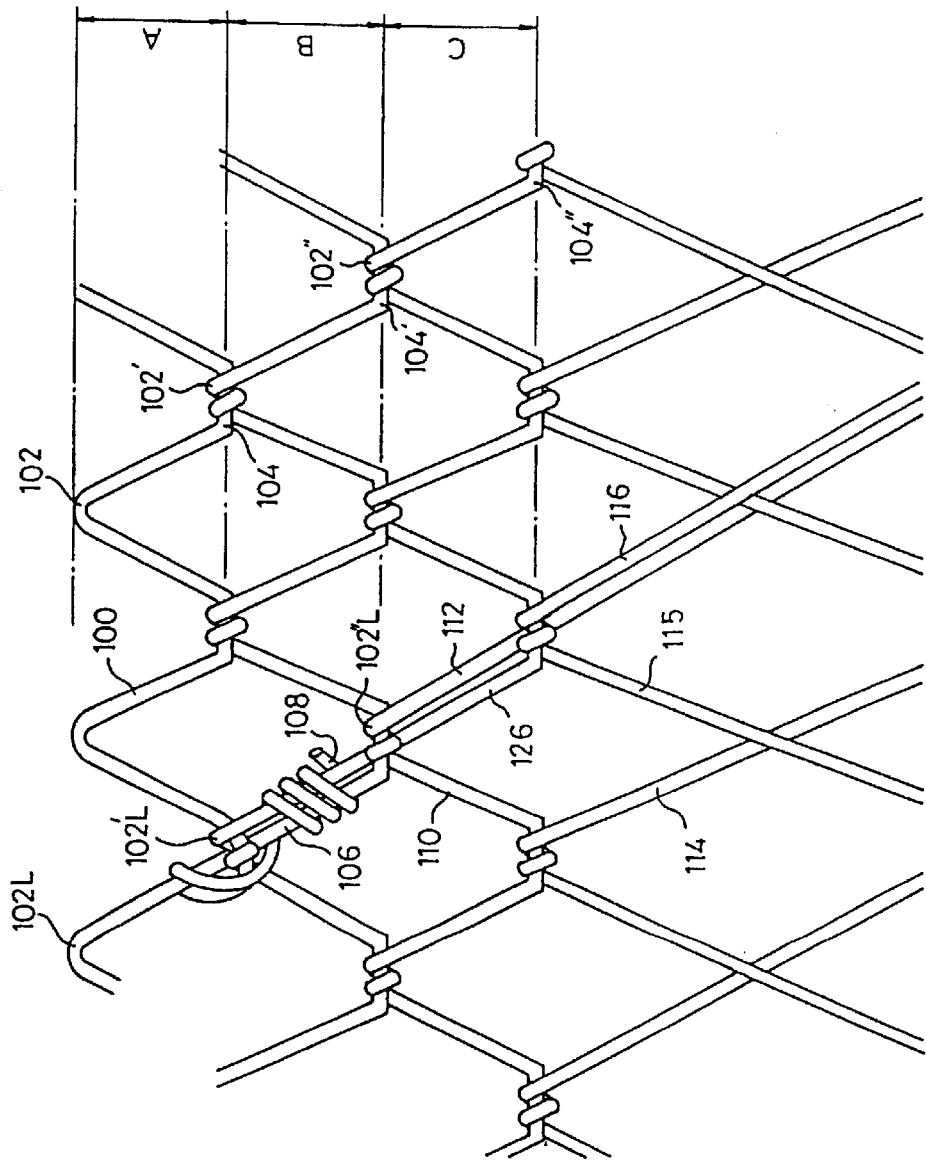
FIG. 12 is a partially detail view showing a zigzag section and a spiral section of FIG. 11.

FIG. 12 shows in detail a portion of the stent according to a third preferred embodiment of the present invention, as will be described below. In particular, referring to a zigzag section shown in FIG. 12, the filament forming a first band A forms a number of peak portions 102 and valley portions 104 along the circumferential direction of the first band. The elongated straight portion 106 forming the last peak portion 102L of the first band A extends downward to form the valley portion 104' of the second band B, and forms a number of peak portions 102' and valley portions 104' in the circumferential direction of the second band B. The peak portions 102' of the second band B are twistedly connected with the valley portions 104 of the first band A.

The elongated straight portion 126 forming the last peak 102'L of the second band B extends downward to form a number of valley portions 104" and peak portions 102" of the third band C in the circumferential direction.

The filament 112 forming the last peak section 102"L of the third band C is twisted with the most upper end valley portion of the zigzag section positioned at the lower end portion of the stent. Of course, according to the method of manufacturing the stent of the present invention, the zigzag section of the upper end portion is first manufactured, and the spiral section in the middle portion is next manufactured. The zigzag section of the lower end portion is manufactured last.

The cylindrical stent according to the first preferred embodiment of the present invention is consisted of a number of bands A, B and C as described above. The stent of first preferred embodiment has elongated straight portions 106 and 126 which are extended downward from the last peak portions 102L and 102L', which is an initial filament of the adjacent lower band, respectively. The stent disclosed in the patent of An et al has no an elongated straight portion extended downward as described above, because the bands are disposed at a given helix angle. Specifically, why the reason the stent of the patent of An et al has no a flat surface perpendicular to the longitudinal axis of the stent is the fact that each of the bands is spirally wound at a given tilt angle to a horizontal plane.

Referring to FIGS. 3 and 4, it will be now described on the manufacturing method of the stent according to the first preferred embodiment of the present invention.

As shown in FIG. 3, the single length of wire is bent in a shape of recess with a number of straight portions 20 so as to form a first band, wherein the initial straight portion 22I of the straight portions 20 is formed to have a constant extended straight portion 8. And, a final straight portion 11F of the first band is not engaged with an initial valley 24I and is extended downward. Although it is not shown in the drawings, a mandrel is generally used on manufacturing the stent, in which the peak and valley portions are bent around pins inserted into holes formed at a regular interval on the periphery of the mandrel.

The straight portion 11F extended downward is bent to form an initial valley portion 24' of an adjacent lower band as shown in FIG. 4. And, the filament is bent to form a number of peak portions 22' and valley portions 24', which forms a second band. Each of the peak portions 22' of the second band is engaged with corresponding one of the valley portions 24 of the first band in such a way of at least one twist, twice times in the embodiment.

The above steps are repeated until the desired cylindrical stent can be achieved. The final straight portion 11F' of a final band is twisted with the initial valley portion of the just adjacent upper band and is finished at a desired position.

Figure 5:
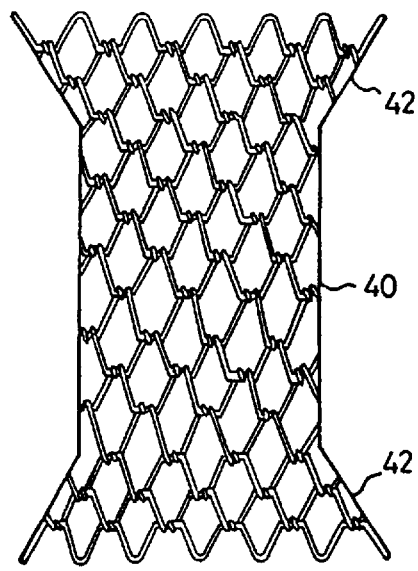
FIGS. 5 and 6 are perspective views showing alternative preferred embodiments of the present invention.
Figure 6:
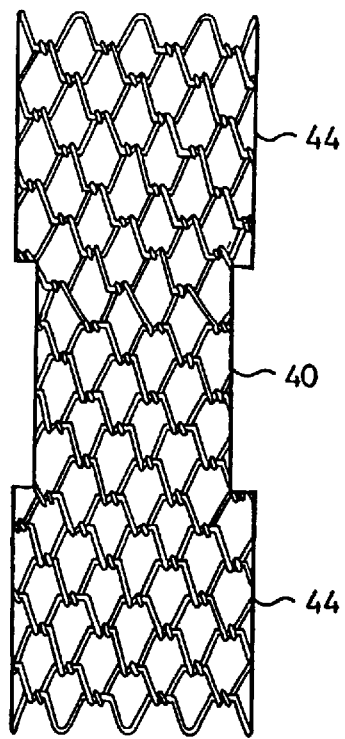

FIGS. 5 and 6 show alternative embodiments of the present invention, of which the elongated straight portions and the final straight portions are not shown for clarity of the drawings. Referring to FIG. 5, both ends of the stents according to the alternative embodiment have a diameter increasing portions 42 in a shape of a flare with the diameter enlarging toward the distal end in order to prevent from migrating. Also, FIG. 6 shows a stent substantially similarly with the alternative embodiment shown in FIG. 5, except that both ends thereof are provided with evenly diameter-enlarging portions 44 having the diameter thereof larger than it of a body 40. Since the zigzag sections of the stent shown in FIGS. 5 and 6 are similar with the zigzag section of the first embodiment, the description thereof will be omitted.

Figure 7:
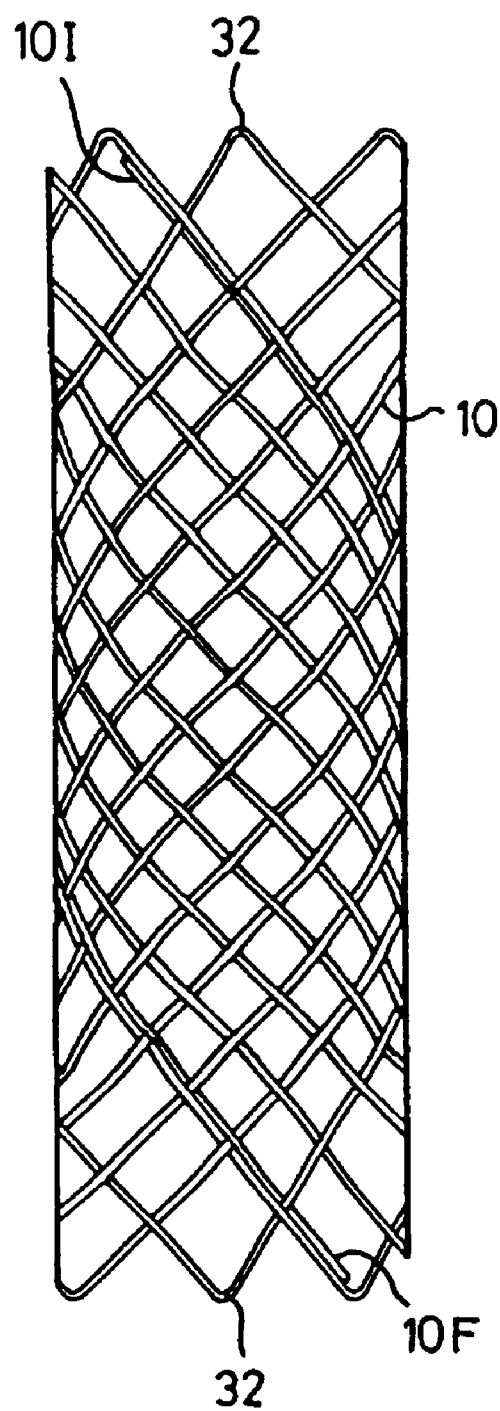
FIG. 7 is a perspective view of a stent according to a second preferred embodiment of the present invention.

FIG. 7 shows a stent according to a second preferred embodiment of the present invention. The stent shown in FIG. 7 uses a single length of filament 10 such as the first embodiment, but the filament is disposed in a shape of a spiral pattern.

Referring to FIG. 7, the stent of the second embodiment has a number of bent points 32 on upper and lower end portions, wherein the number of the bent points of the upper end portion is identical to the number of the bent points of the lower end portion. The filament consisting a body portion cross spirally in an unengaged manner. One segment of filament runs alternatively on and under other segments which are disposed in a direction opposite to that of the segment, so that a number of meshes are formed by the crossing points of the segments. Initial segment 10I and final segment 10F are cut and remain in free ends so as to not protrude outwardly.

Figure 8:
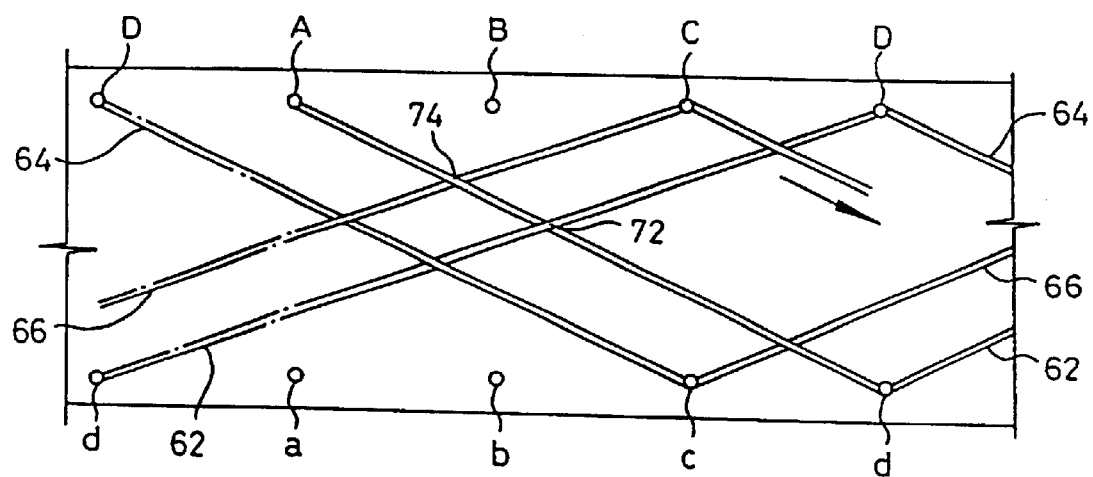
FIG. 8 is a view showing the manufacturing process of the stent of the second embodiment.

Referring to FIG. 8, which shows the developed peripheral of a mandrel to easily understand, it will be described on a method of manufacturing the stent according to the second embodiment of the present invention. The mandrel is attached on the upper and lower ends with each four pins A, B, C and D, and a, b, c and d, but is not limited thereto, in order to manufacture the stent.

Because the stent of the second embodiment is made of a single length of a filament, the only one end of the initial filament is secured with a cramp (not shown) of the mandrel. In the stent of the second embodiment, the filament starts with the pin A. The filament started from the pin A runs spirally along the mandrel and turns around one of pins a, b, c, and d on the lower end. At that time, the pin of the lower end to which the filament is reached may be determined depending upon a given spiral angle, and it does not matter that the filament will be reached to other of the pins b, c, and d on the lower end by changing the spiral angle.

It will be described on the case that the filament is reached to the pin d in ¾ turnings in the embodiment. The filament, which starts from the pin A and reaches to the pin d as described above, turns around the pin d and runs a point 62 toward the upper. The choice of the pin on the upper end, at which the filament departed from the pin d is reached, will be depending on the designer, but it does not matter if the filament runs evenly all of the pins with it being wounded repeatedly to the upper and lower ends.

In this embodiment, the filament passed through the pin d reaches the pin D at the upper end after fully rotating the mandrel. The filament passed through the pin D passes through the pin c at the lower end after rotating ¾ of the mandrel, and passes through the pin C at the upper end after fully rotating the mandrel. In other words, the points 62, 64 and 66 illustrated on the right side in FIG. 8 are positioned at the same spot as the points 62, 64 and 66 illustrated on the left side in FIG. 8. The filament reaches the pin A by passing through the pins b, B and a.

The filaments form a number of crossing points such as 72 and 74 while crossing one another by repeating the above processes. The filaments form a stable structure by crossing one another. When a filament crosses under another filament at a crossing point, the latter should be slightly lifted at the crossing point by means of an apparatus such as a "-" shaped driver or a knitting needle so that the former can smoothly pass under the latter, as in the method of knitting.

When the filament returns to its starting point after passing through all the pins, the circumferential parts of the stent should be released to form a desirable diameter of the stent. Upon completion of the above processes, all the pins are removed from the mandrel to discharge the stent from the mandrel.

The process of manufacturing the stent according to the second embodiment described above standardized a case wherein four pairs of pins are mounted on the upper and lower ends, respectively, to assist in understanding. However, the same stent can be manufactured regardless of the number of pins. For instance, if ten pins are employed, a filament starts from the starting point and fully rotates the mandrel once, twice and ⅗ of the mandrel. The filament then reaches a predetermined pin at the lower end, and rotates the mandrel in the counter direction for appropriate times, and lapse three pins from the pin at the starting point. Through these processes, the filament passes through all of the ten pins.

If the number of pins is odd such as nine or eleven, the filament will not periodically cross at some points. However, the number of pin intervals, at which the filament will pass, can be variously adjusted to be two or three, etc.

Figure 9:
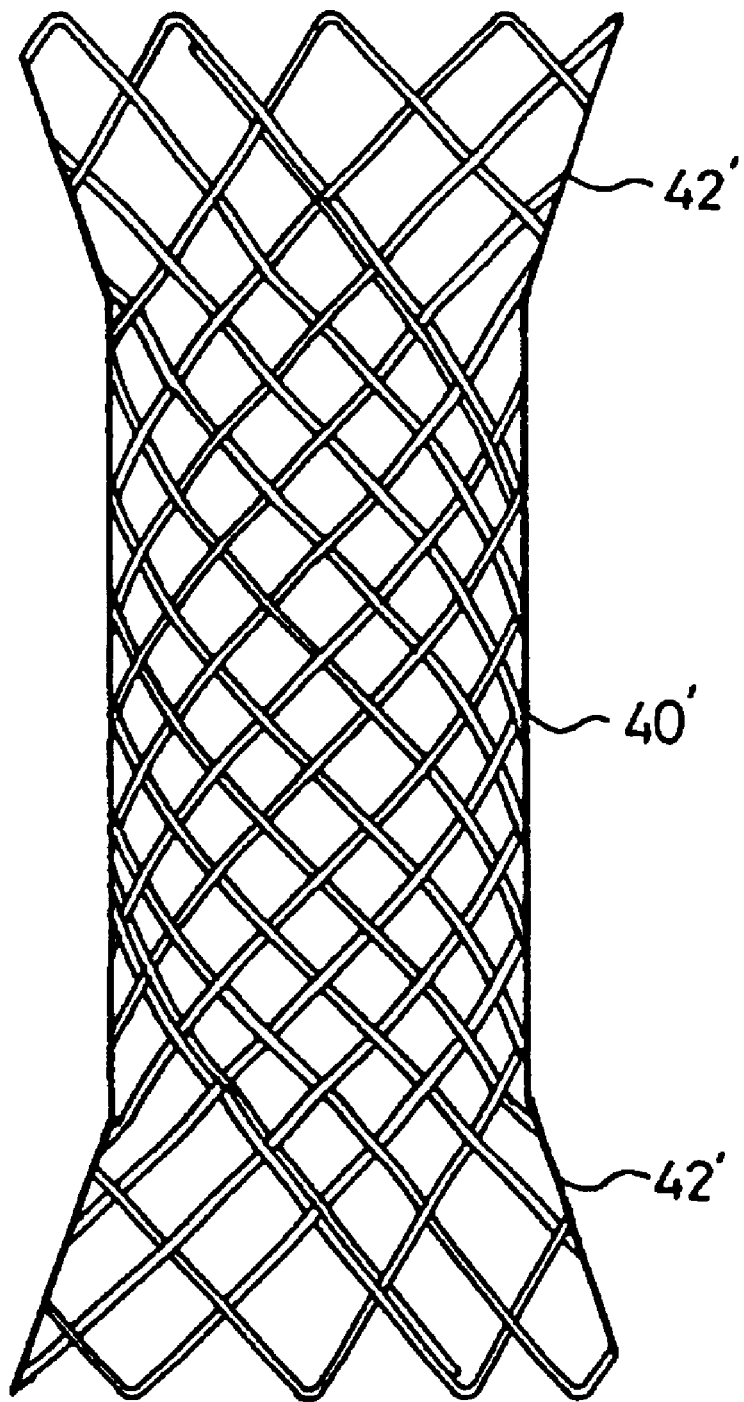
FIGS. 9 and 10 are perspective views showing further alternative preferred embodiments of the present invention.
Figure 10:
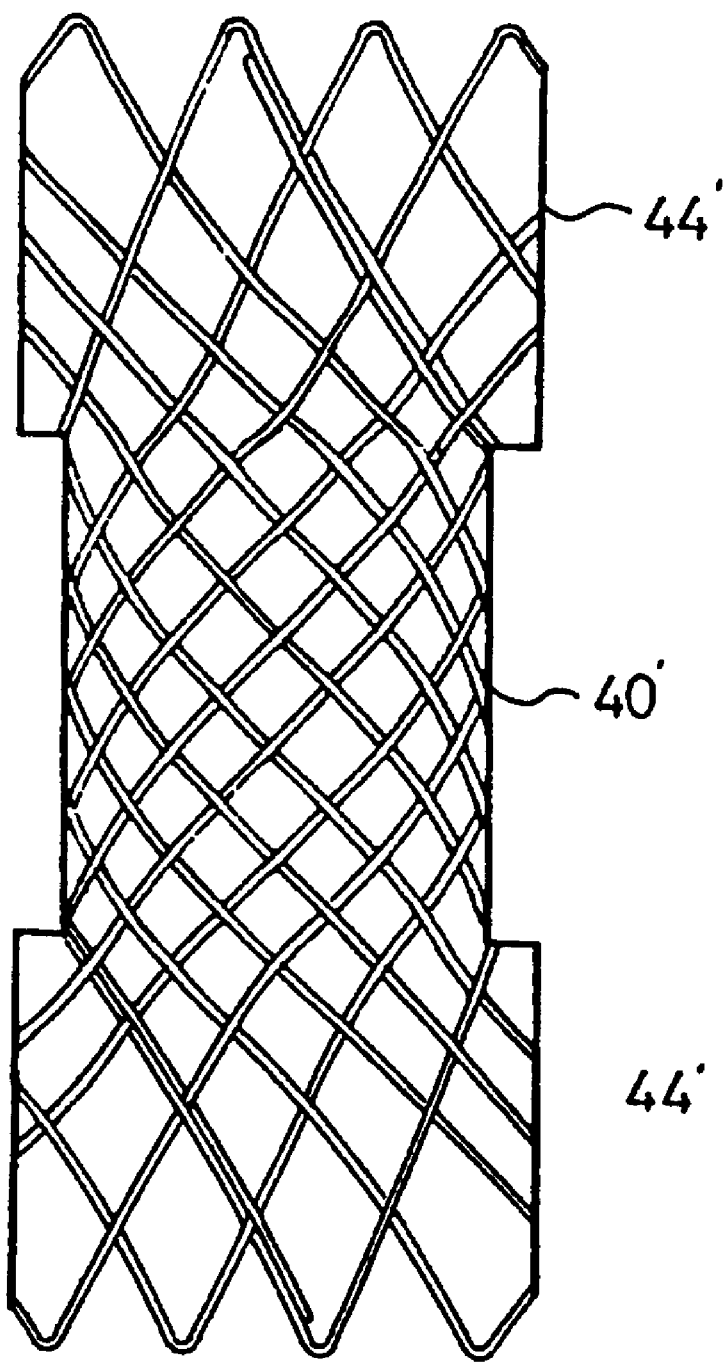

FIGS. 9 and 10 illustrate another alternative embodiment of the present invention. Referring to FIG. 9, the stent according to another alternative embodiment of the present invention has diameter-enlarged portions 42', 42' at both end parts, the diameters of which are extended toward the ends so that the stent may not slide off. Also, FIG. 10 illustrates a stent which is substantially identical with the alternative varied embodiment illustrated in FIG. 9 except that it has portions 44', 44' at both end, the diameters of which are larger than the diameter of the main body 40. Since the spiral part of the stent illustrated in FIGS. 9 and 10 is substantially identical with that illustrated in the second embodiment, no further explanation will be provided.

Figure 11:
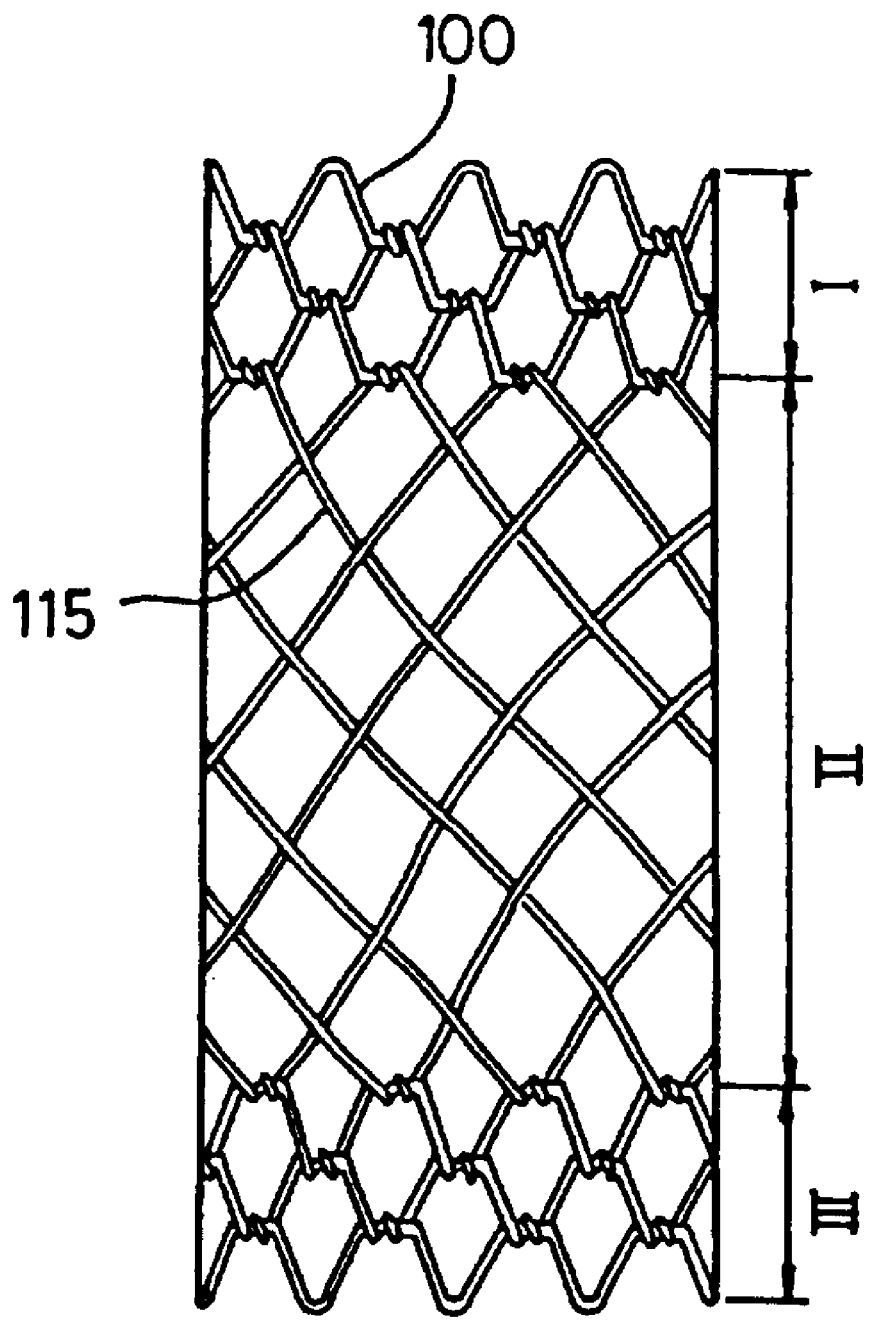
FIG. 11 is a perspective view of a stent according to a third preferred embodiment of the present invention.

FIG. 11 briefly illustrates a cylindrical stent according to a third embodiment of the present invention. The stent in FIG. 11 comprises a filament of a single line, including zigzag sections I and III at both end portions and a spiral section II in the middle portion. However, a person skilled in the art will know that another zigzag section can be additionally formed at the middle portion of the spiral part positioned between both end portions of the stent.

FIG. 12 further illustrates a part of the stent according to the third embodiment of the present invention illustrated in FIG. 11. The zigzag section I positioned at an upper end of the stent comprises a plurality of straight portions 100, peak portions 102, and valley portions 104 integrally engaged with the straight portions. The straight portions 100, peak portions 102 and the valley portions 104 distributed on a common plane form a band (A, B or C). In the embodiment illustrated in FIG. 12, each of the zigzag sections I and III positioned at the upper and lower end portions of the stent comprises three bands, respectively, but is not limited thereto.

A series of bands A, B, C are connected to one another by twisting the valley portions of the upper adjacent band with the peak portions of the lower adjacent band. To ease such twisting, and to prevent a possible change in a configuration of the stent when expanding or shrinking, the tops of the valley portions take the form of a straight line.

Referring to FIG. 12, a filament 114 forming the spiral section II in the middle portion of the stent is twisted with the valley portion 104" of the lowest band C of the zigzag section I. The spiral section II comprises a filament 112 extending toward the last peak portion 102"L of the lowest band C of the zigzag section I positioned at an upper end portion of the stent, and is twisted with the valley portion 104" of the most upper band A of the zigzag section III positioned at the lower end portion of the stent. The filament 112 is also twisted with another valley portion 104" of the lowest band C of the zigzag section I positioned at the upper end portion of the stent. The filaments 114 forming the spiral section II cross one another without being twisted at the crossing points.

Filaments of a single line are employed according to one aspect of the present invention. Therefore, the stent for expanding the vascular has only two ends 108 connected to the band of the zigzag sections positioned on the upper and lower end portions. Thus, loading the stent toward its radial direction will change neither its configuration nor result in damage of tissues of the vascular.

The filament forming a first band A forms a number of peak portions 102 and valley portions 104 along the circumferential direction of the first band. The elongated straight portion 106 forming the last peak portion 102L of the first band A extends downward to form the valley portion 104' of the second band B, and forms a number of peak portions 102' and valley portions 104' in the circumferential direction of the second band B. The peak portions 102' of the second band B are twistedly connected with the valley portions 104 of the first band A.

The elongated straight portion 126 forming the last peak 102'L of the second band B extends downward to form a number of valley portions 104" and peak portions 102" of the third band C in the circumferential direction.

The filament 112 forming the last peak section 102"L of the third band C is twisted with the most upper end valley portion of the zigzag section positioned at the lower end portion of the stent. Of course, according to the method of manufacturing the stent of the present invention, the zigzag section of the upper end portion is first manufactured, and the spiral section in the middle portion is next manufactured. The zigzag section of the lower end portion is manufactured last.

In the spiral part II, the filament 114 facing the lower end portion of the stent extends toward the direction opposite to the filament 115 facing the upper end portion of the stent. If these filaments 114, 115 are twisted in the spiral form, a plurality of meshes are formed by the crossing points of the filaments.

The last filament 116 of the twisted filaments extends toward the lower end portion of the stent after being twisted with the valley porion 104" of the band C. The filament 116 extending toward the lower end portion forms the zigzag section III at the lower end portion.

The end 108 forming the starting point of the first band A is twisted with the fixed filament at a predetermined point. The embodiment in FIG. 12 shows that the end 108 is twisted with the extended filament of the first band and the second band, but is not limited thereto.

The upper part of the stent for expanding a lumen of a body has been explained with reference to FIG. 12. Since the zigzag section III positioned at the lower end portion of the stent is substantially identical with the zigzag section I described above in terms of configuration and structure, no further explanation will be provided.

In the embodiments of the present invention, both end portions of the stent include a pair of zigzag sections comprising a plurality of bands twistedly connected to one another, thereby having low flexibility but high restorability. The spiral section in the middle portion is arranged such that the filaments are not twisted one another, thereby having low restorability but high flexibility.

The stent according to an alternative embodiment of the present invention will now be explained with reference to FIG. 13.

Figure 13:
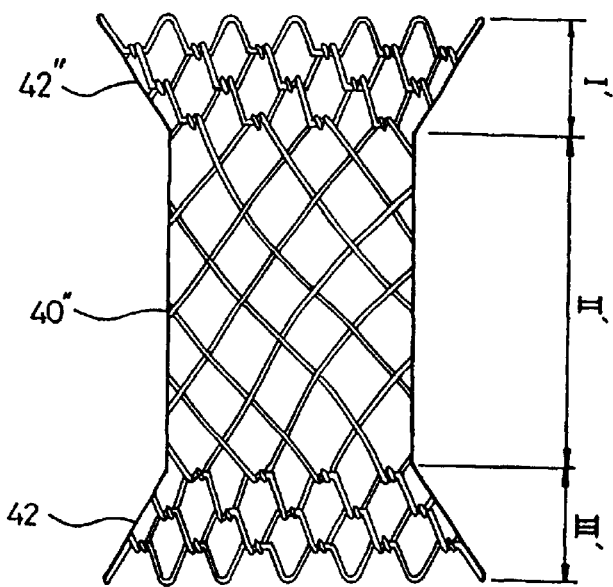
FIGS. 13 and 14 are perspective views of still further alternative preferred embodiment of the present invention.

The stent for expanding body lumens illustrated in FIG. 13 is substantially identical with the embodiment illustrated in FIGS. 11 and 12 except that the zigzag sections I' and III' formed at both end portions to prevent sliding off of the stent are extended in the form of a flare.

The zigzag sections I' and III' taking the form of a flare are positioned on the left and right sides of the spiral section in the middle portion prevents the stent from migrating. Also, even if the stent is disposed within a curved body lumen, the spiral section in the middle portion can be sufficiently bent, and the zigzag sections I' and III' on the left and right sides help restoring the original configuration of the stent. Also, both end portions extended in the form of a flare prevent the stent from migrating in the curved lumen.

Figure 14:
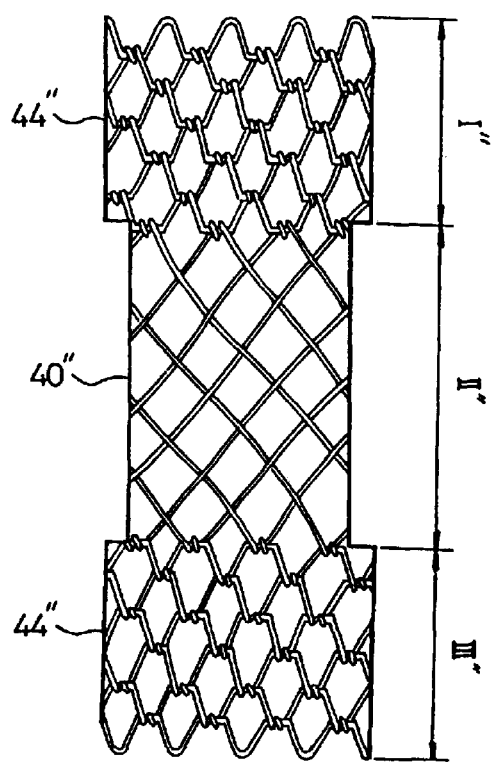

FIG. 14 illustrates a stent according to another alternative embodiment of the present invention. The stent in FIG. 14 has zigzag sections I" and III", the diameters of which are evenly extended toward both ends of the stent, to more strongly prevent the stent from migrating when disposed within a body lumen than that in FIG. 13.

As described above, according to the third embodiment and its alternative embodiment of the present invention, the stent for expanding a lumen of a body comprises zigzag sections at both end portions thereof and a spiral section in the middle portion, thereby taking both advantages of the zigzag sections of high restorability and a spiral section of high flexibility. Therefore, the stent according to the embodiment can maintain an open state of the central part even if it is disposed within a curved lumen by such a catheter owing to the zigzag sections formed at both end portions and maintain restorability thereof.

Also, the stent for expanding a lumen of a body described above has a greater size of diameters in the zigzag sections than that of the spiral section, thereby preventing the stent from sliding off the target site of the lumen.

The material used for the stent for expanding a lumen of a body described above has been widely known.

Although a number of materials are suggested, including Ni—Ti alloys of 49 to 58%(atm) nickel, Ni—Ti alloys in which the transformation between austenite and martensite is complete at a temperature of 10° C. or below are preferable. In the unstressed state at room temperature, such super elastic materials occur in the austenite crystallin crystalline phase and, upon application of stress, exhibit stress-induced austenite-martensite (SIM) crystalline transformations which produce nonlinear elastic behavior.

Also, it is suggested the stent made up of a shape memory alloy such as the nickel-titanium alloy known as nitinol to allow the shape memory alloy member to recover its original shape upon being warmed by body temperature or a warming fluid supplied by a fluid injection apparatus.

Though not illustrated in the drawings, a wrapping process may be employed to prevent cells from growing through the mesh structure of the stent. The wrapping process comprises surrounding the stent with meshes composed of nylon, and coating the stent with a hose-type thin film composed of polymer or silicon rubber, etc. Such structure has been disclosed in the International Publication No. WO 92/06734 and U.S. Pat. No. 5,330,500, which the contents are incorporated into the present application.

Figure 15:
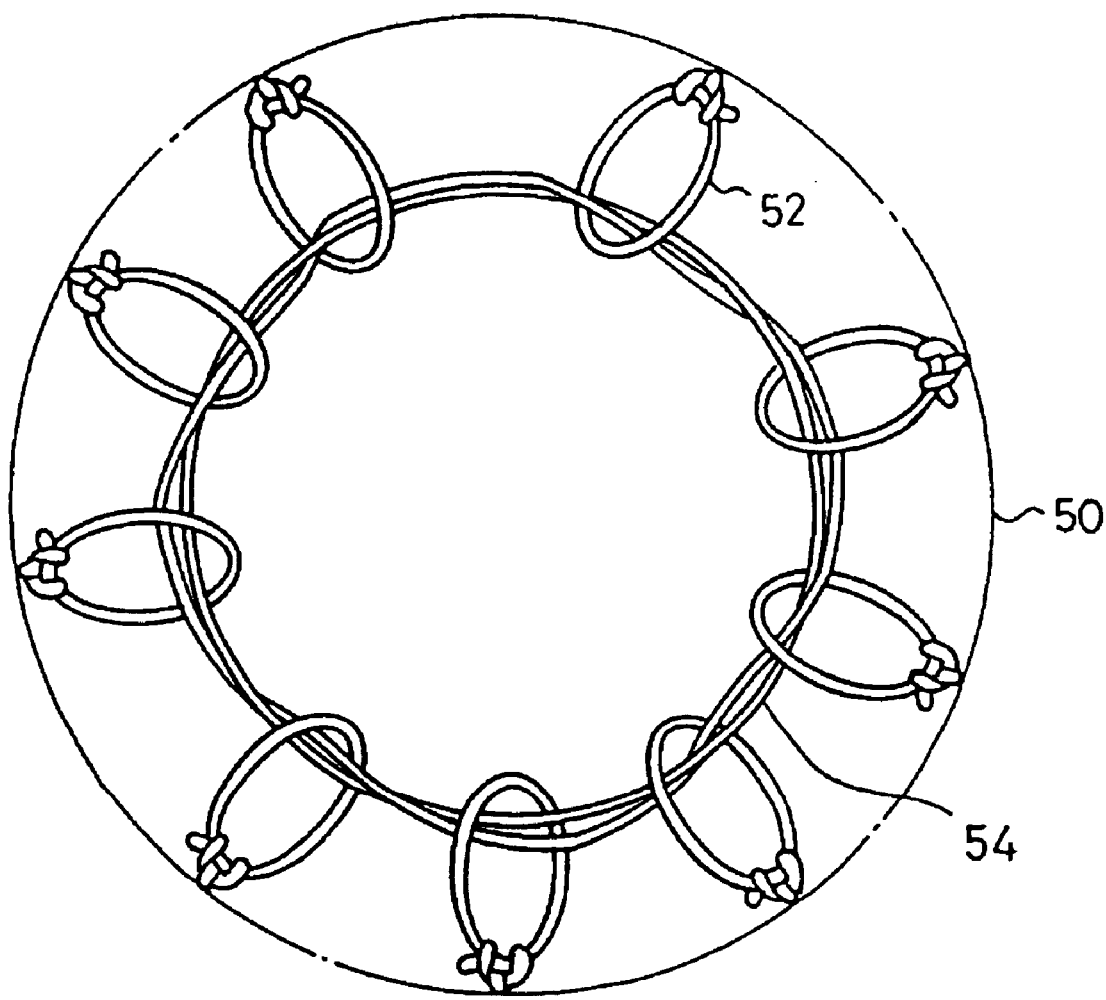
FIG. 15 is a perspective view showing a retrieving means provided within the one end of the stent.

FIG. 15 briefly illustrates a retrieving member for retrieving the stent after treating the disease in a body lumen. The retrieving member, which is generally provided inside one end portion of the stent, comprises a plurality of fixed nylon wires 52 connected to the filament arranged along the circumferential direction of the stent 50, and retrieving nylon wires 54 supported by the fixed wires 52. The wires 52, 54 are preferably composed of a line of high intensity such as a fishing line.

While the present invention has been described and illustrated herein with reference to the preferred embodiments thereof, it will be understood by those skilled in the art that various changes in form and details may be made therein without departing from the spirit and scope of the invention.

What is claimed is:

1. A stent for expanding a lumen of a body, the stent being made up of a single length of a filament and including a plurality of bands formed in a zigzag pattern, wherein:
    each of the bands includes a series of straight portions, peak portions, and valley portions, the peak and valley portions being integrally engaged with the straight portions, and each of the bands being disposed along a circumferential direction of the stent on a plane substantially perpendicular to a longitudinal axis of the stent;
    each peak portion that is adjacent to another band being twisted with a respective valley portion of the other band; and
    an initial portion of each band other than an initial band being an extension from a last straight portion of a previous adjacent band.

2. The stent as claimed in claim 1, wherein upper and lower end portions of the stent have a flare shape in which a diameter is increased toward a distal end thereof to prevent the stent from migrating inside the lumen.

3. The stent as claimed in claim 1, wherein the upper and lower end portions of the stent have a larger diameter than a middle portion of the stent.

4. The stent as claimed in claim 1, wherein the filament is made of a Ni—Ti alloy.

5. The stent as claimed in claim 1, wherein the stent is covered or wrapped with a flexible material.

6. The stent as claimed in claim 1, further comprising on one end thereof a retrieving member by which the stent is removed from the lumen.

7. The stent as claimed in claim 6, wherein the retrieving member comprises a plurality of wires attached to the one end of the stent.

8. The stent as claimed in claim 1 wherein said each peak portion is twisted at least once around the respective valley portion of the other band.

9. The stent as claimed in claim 1 wherein said each peak portion is twisted with a single respective valley portion of the other band.

10. A stent for expanding a lumen of a body, the stent being made of a single length of a filament, the stent comprising:
    a body portion formed in such a way that the filament crosses in a spiral pattern to form a plurality of segments with the segments being not engaged with each other; and
    upper and lower end portions having a plurality of bent points;
    wherein the number of the bent points of the upper end portion is equal with the number of the bent points of the lower end portion, and any one segment passes alternately on and under other segments which are wound along a longitudinal axis of the stent in a spiral direction so that cross points of the segments form a plurality of meshes.

11. The stent as claimed in claim 10, wherein the upper and lower end portions of the stent have a flare shape in which a diameter is increased toward a distal end thereof to prevent the stent from migrating inside the lumen.

12. The stent as claimed in claim 10, wherein the upper and lower end portions of the stent have a larger diameter than a middle portion of the stent.

13. The stent as claimed in claim 10, wherein the filament is made of a Ni—Ti alloy.

14. The stent as claimed in claim 10, wherein the stent is covered or wrapped with a flexible material.

15. The stent as claimed in claim 10, further comprising on one end a retrieving member by which the stent is removed from the lumen.

16. The stent as claimed in claim 15, wherein the retrieving member comprises a plurality of wires attached to the one end of the stent.

17. A stent for expanding a lumen of a body, the stent being made from a single length of filament, the stent comprising:

zigzag sections, in which the filament is wound in a zigzag manner, disposed on both end portions of the stent, each of the zigzag sections including a plurality of bands, each of the bands including alternate peaks and valleys, each peak of one band being twisted together with a single respective valley of an adjacent band; and a spiral section, in which the filament is wound in a spiral manner, disposed between the zigzag sections.

18. A stent for expanding a lumen of a body, the stent being made of a single length of filament, the stent comprising:

zigzag sections, in which the filament is wound in a zigzag manner, disposed on both end portions of the stent, each of the zigzag sections including a plurality of bands, each of the bands including a series of straight portions, peak portions, and valley portions, the peak and valley portions being integrally engaged with the straight portions, each of the bands being disposed along a circumferential direction of the stent on a plane substantially perpendicular to a longitudinal axis thereof, and each valley portion of the bands being twisted with a peak portion of an adjacent band; and a spiral section, in which the filament is wound in a spiral manner, disposed between the zigzag sections.

19. A stent for expanding a lumen of a body, the stent being made of a single length of filament, the stent comprising:

zigzag sections, in which the filament is wound in a zigzag manner, disposed on both end portions of the stent; and a spiral section, in which the filament is wound in a spiral manner, disposed between the zigzag sections, the spiral section including, a body portion formed in such a way that the filament crosses in a spiral pattern to form a plurality of unengaged segments, and upper and lower end portions having a plurality of bent points.

20. A stent for expanding a lumen of a body, comprising:

bands constructed from a single length of a filament;

each of the bands including alternate peaks and valleys; and each peak of one band being twisted together with a single respective valley of an adjacent band.

21. The stent of claim 20 wherein the bands are cylindrical.

22. The stent of claim 20 wherein each of the bands includes straight portions of the filament respectively disposed between each peak and each respective adjacent valley.

23. The stent of claim 20 wherein each of the valleys comprises a respective straight portion of the filament.

24. The stent of claim 20 wherein each peak of one band is twisted at least once around the single respective valley of the adjacent band.

25. The stent of claim 20, further comprising:

a mid portion having first and second opposite sides;

a first end portion connected to the first side of the mid portion;

a second end portion connected to the second side of the mid portion;

wherein the bands are cylindrical and have respective diameters; and wherein bands that compose the first and second end portions have respective diameters that are larger than the diameter of a band that composes the mid portion.

26. The stent as claimed in claim 17, further comprising a zigzag section formed in a middle portion of the spiral section.

27. The stent as claimed in claim 17, wherein the end portions of the stent have a flare shape in which a diameter is increased toward a distal end thereof to prevent the stent from migrating inside the lumen.

28. The stent as claimed in claim 17, wherein the end portions of the stent have a larger diameter than a middle portion of the stent.

29. The stent as claimed in claim 17, wherein the filament is made of a Ni—Ti alloy.

30. The stent as claimed in claim 17, wherein the stent is covered or wrapped with a flexible material.

31. The stent as claimed in claim 17, further comprising on one end a retrieving member by which the stent is removed from the lumen.

32. The stent as claimed in claim 24, wherein the retrieving member comprises a plurality of wires attached to the one end of the stent.

* * * * *

UNITED STATES PATENT AND TRADEMARK OFFICE
CERTIFICATE OF CORRECTION

PATENT NO. : 6,241,757 B1      Page 1 of 1
DATED : June 5, 2001
INVENTOR(S) : Sung Soon An, Chel Seng Kim, Sung Pil Choi, Tae Hyung Kim, Ho Young Song, Sang Woo Song It is certified that error appears in the above-identified patent and that said Letters Patent is hereby corrected as shown below:

Column 12, claim 32,
Line 46, please delete "24" and insert -- 31 --.

Signed and Sealed this

Fifth Day of March, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,241,757 B1
DATED         : June 5, 2001
INVENTOR(S)   : Sung Soon An, Chel Seng Kim, Sung Pil Choi, Tae Hyung Kim, Ho Young Song and Sang Woo Song It is certified that error appears in the above-identified patent and that said Letters Patent is hereby corrected as shown below:

<u>Title page,</u>
Item [73], Assignee should read -- Stentech Inc. and Ho Young Song, Seoul (KR) --

Signed and Sealed this

First Day of October, 2002

*Attest:*

*Attesting Officer*

JAMES E. ROGAN
*Director of the United States Patent and Trademark Office*